United States Patent
Ingenhoven et al.

(10) Patent No.: US 6,824,024 B2
(45) Date of Patent: Nov. 30, 2004

(54) DEVICE FOR THE TAKE-UP AND/OR RELEASE OF LIQUID SAMPLES

(75) Inventors: Nikolaus Ingenhoven, Männedorf (CH); Noa Schmid, Grabs (CH)

(73) Assignee: Tecan Trading AG, Mannedorf (CH)

(*) Notice: Subject to any disclaimer, the term of this patent is extended or adjusted under 35 U.S.C. 154(b) by 0 days.

(21) Appl. No.: 10/416,785
(22) PCT Filed: Nov. 15, 2001
(86) PCT No.: PCT/CH01/00672
§ 371 (c)(1), (2), (4) Date: Oct. 24, 2003
(87) PCT Pub. No.: WO02/40163
PCT Pub. Date: May 23, 2002

(65) Prior Publication Data
US 2004/0050866 A1 Mar. 18, 2004

(30) Foreign Application Priority Data
Nov. 17, 2000 (CH) .............................. 2252/00
Nov. 29, 2000 (CH) .............................. 2314/00

(51) Int. Cl.⁷ .............................................. B67D 3/00
(52) U.S. Cl. .................. 222/504; 222/509; 222/524; 422/99; 422/100; 73/864.01
(58) Field of Search ................ 222/1, 504, 509–510, 222/420, 524, 525, 482, 478, 386; 422/99–100; 73/864.01, 864.11, 864.33, 863.32

(56) References Cited

U.S. PATENT DOCUMENTS

| 4,087,248 A | 5/1978 | Miles |
| 5,763,278 A | * 6/1998 | Sickinger et al. ........... 436/180 |
| 5,916,524 A | * 6/1999 | Tisone ........................ 422/100 |
| 6,024,925 A | 2/2000 | Koester |
| 6,599,479 B1 | * 7/2003 | Kietzmann et al. ......... 422/100 |
| 6,713,021 B1 | * 3/2004 | Shvets et al. ................ 422/100 |

FOREIGN PATENT DOCUMENTS

| DE | 43 18 919 A | 12/1994 | |
| DE | 4318919 A1 | * 12/1994 | ............ G01N/1/14 |
| DE | 198 27 293 A | 12/1999 | |
| WO | WO 97 15394 | 5/1997 | |
| WO | WO-97/15394 | * 5/1997 | ............. B01L/3/00 |

* cited by examiner

Primary Examiner—Gene Mancene
Assistant Examiner—Frederick C. Nicolas
(74) Attorney, Agent, or Firm—Notaro & Michalos PC (57) ABSTRACT

A device for aspirating and/or dispensing liquid samples has a hollow body with a cavity for the liquid. A movement element for aspirating and/or dispensing the liquid is moved by a movement unit having a first drive element driven by a first drive. A pipette tip or adapter therefor, receives liquid from the cavity over a line, and a flush line discharges into the cavity. A carrier unit movably carries the movement unit in at least one spatial axis and includes at least one second drive element driven by a second drive. The movement unit includes the hollow body, the movement element, the first drive element, the second drive element and the pipette tip or adapter, as well as a pulse generator for generating pressure waves in the liquid in the cavity during dispensing, all these elements being movable together with respect to the carrier unit.

24 Claims, 4 Drawing Sheets

DEVICE FOR THE TAKE-UP AND/OR RELEASE OF LIQUID SAMPLES

The present invention relates to a device for taking up and/or releasing liquid samples according to the preamble of independent claim 1 and systems which include one or more such devices.

It is known that droplets with a volume of more than 10 µl can be dispensed from the air very easily, since if the pipette is correctly manipulated, the droplets leave the pipette tip of their own accord. The droplet size is then determined by the physical properties of the sample liquid, such as surface tension or viscosity. The droplet size thus limits the resolution of the quantity of liquid to be dispensed.

The aspirating and dispensing, i.e. the pipetting of liquid samples with a volume of less than 10 µl, in contrast, typically requires instruments and techniques which guarantee the dispensing of such small samples. The dispensing of a liquid using a pipette tip, i.e. using the endpiece of a device for aspirating and/or dispensing sample liquid, can occur from the air ("from air") or by touching a surface. This surface can be the solid surface of a container ("on tip touch"), into which the liquid sample is to be dispensed. It can also be the surface of a liquid in this container ("on liquid surface"). A mixing procedure following the dispensing is recommended—particularly for very small sample volumes in the nanoliter or even picoliter range—so that uniform distribution of the sample volume in a reaction liquid is ensured.

Disposable tips significantly reduce the danger of unintentional transfer of parts of the sample into a container (contamination). Simple disposable tips are known ("air-displacement tips"), whose geometry and material is optimized for the exact aspiration and/or dispensing of very small volumes. The use of so-called "positive-displacement tips", which have a pump plunger inside, is also known. Two procedures must be differentiated from one another for the automation of the pipetting process of volumes less than 10 µl: the defined take-up (aspiration) and the subsequent release (dispensing) of liquid samples. The pipette tips are typically moved by the experimenter or a machine between these procedures, so that the aspiration location of a liquid sample is often different from its dispensing location. Only the liquid system, which includes a pump (for example a diluter implemented as a syringe pump), liquid line, and endpiece (pipette tip), is essential for the correctness and reproducibility of aspiration and/or dispensing.

A device and a corresponding method are known from U.S. Pat. No. 5,763,278. They involve automatic pipetting of small volumes, the device including a pipetting needle, a diluter with a liquid outlet having a syringe, and a valve. The syringe includes a piston and a piston drive. A line connects the needle and the liquid outlet of the diluter, the diluter and the line containing an essentially incompressible liquid. A pulse generator is positioned in the device and connected to the incompressible liquid in the line so that mechanical pulses with a force of at least 0.01 Ns can be emitted directly into the liquid of the line. A pulse of this type is used to drive liquid out of the needle. The droplet size is defined by a targeted advance of the diluter piston and the droplet is ejected from the needle using a pulse. Because the volume is defined using the diluter, the droplet size and its reproducibility is a function of the resolution of the diluter and is limited thereby.

A pipetting device which includes a piston pump and a pulse generator in the form of a piezoelectric element is known from Japanese Patent 09 327628. The piezoelectric element is also the front plate of the piston and is used for terminating the dispensing procedure. The piston causes the majority of the liquid dispensing through its downward movement and is blocked during the actuation of the piezoelectric plate. The movement direction of the piezoelectric plate corresponds in this case to that of the piston. At least a part of the volume dispensed thus always depends on the movement of the piston, so that the reproducibility of the piston movement limits the resolution of the pipetting device.

From WO 97/15394 a multiwellplate called there as "JetWell" is known with wells that have an larger upper opening and a nozzle-like opening below. When a pressure pulse is exercised to the surface, a jet of liquid is ejected through each one of these nozzles. Selecting the duration of such a pressure pulse defines the volume of the ejected liquid. Larger volumina cannot be pipetted or dispensed this way.

A sample dosage system, according to the species, comprising an injection needle which is linked to a stationary dosage pump as well as to an also stationary liquid reservoir is known from DE 43 18 919. A sample dosage system for being applied to liquid chromatography is disclosed. This system comprises switching means with which it is possible—in a first position of the switching means and by closing the injection needle—to make a connection between the liquid reservoir and the dosage pump. In a second position of the switching means it is possible to lift off the injection needle and to separate the reservoir for the flushing fluid from the dosage pumpe. This switching means are implemented basically as some sort of three-way valves and provide for the flushing of the injection needle and—by pulling back the piston—also of the cylinder.

The object of the present invention is to suggest an alternative device of the type initially cited for aspirating and/or dispensing liquid samples down into the picoliter range, which allows the flushing of the cavity via a flush inlet which is independent of the pipette tip.

This object is achieved according to the present invention in that a device for aspirating and/or dispensing liquid samples is suggested which corresponds to the features of independent claim 1. Further preferred features result from the dependent claims.

Such a device for aspirating and/or dispensing liquid samples has the advantage that it may be constructed in a very space-saving way, so that a system for aspirating and/or dispensing samples of a liquid may include one single device, but preferably many such devices, which may be positioned in linear groups or in two-dimensional arrays. Such systems are preferably automated and therefore capable of processing large numbers of samples. For the purpose of rationalizing the cycles, such systems are preferably equipped with a robot device which may move the devices in the X and/or Y and/or Z directions. Due to the multiple devices arranged in an array, the liquid samples may be dispensed at the "wells" of microplates, which are also known as microtitration plates (trademark of Beckman Coulter, Inc. 4300 N. Harbour Blvd., P.O. Box 3100 Fullerton, Calif. 92834, USA).

Preferred and exemplary embodiments of the device according to the present invention for aspirating and/or dispensing liquid samples are described in greater detail in the following on the basis of a schematic drawing—which is merely to illustrate the present invention, but not restrict its scope.

Figure 1:
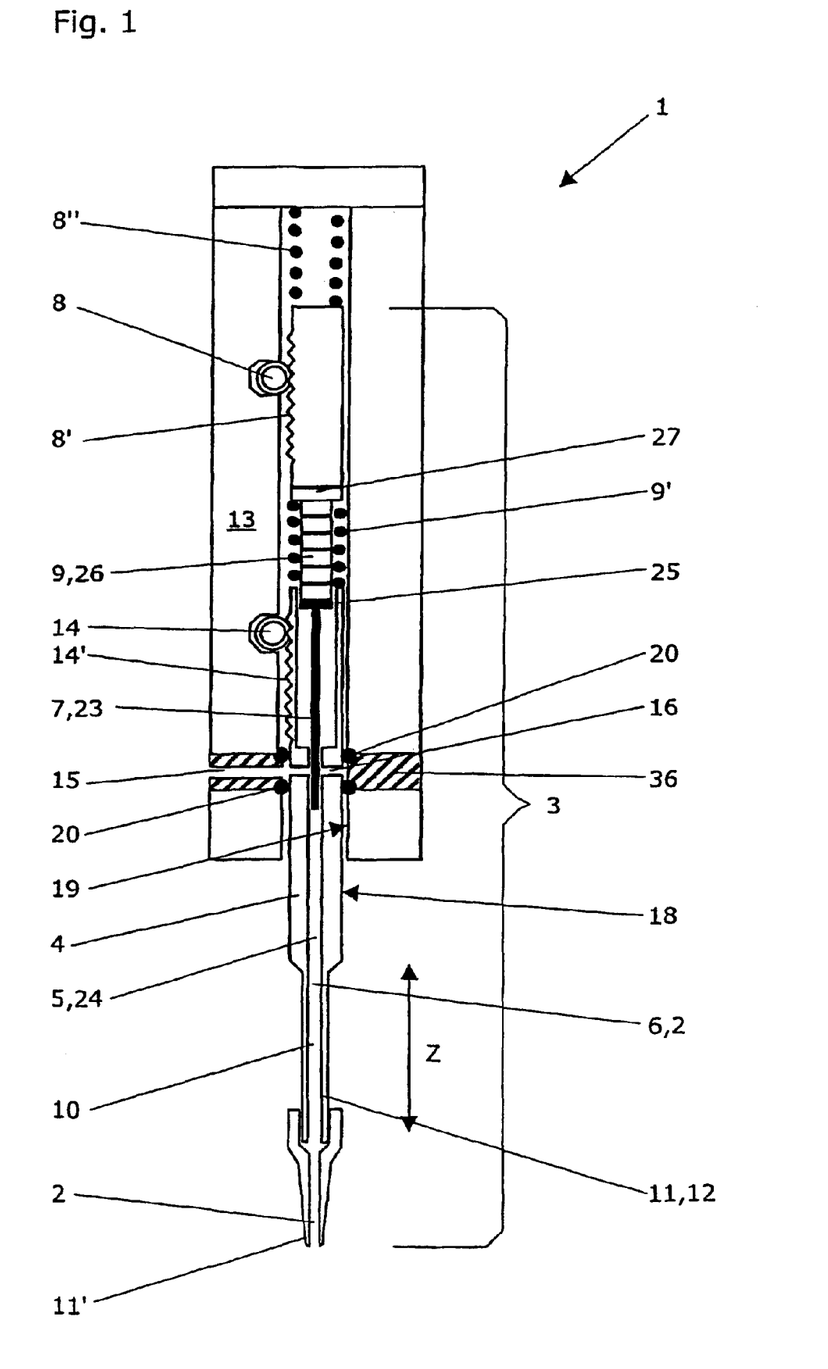
FIG. 1 shows a device for aspirating and/or dispensing liquid samples according to a first embodiment.

FIG. 1 shows a device according to the present invention for taking up and/or releasing liquid samples, according to a first embodiment. This device 1 is used for taking up and/or releasing samples of a liquid 2 and therefore for dispensing and/or pipetting such liquids. This device 1 includes a movement unit 3, which in turn includes a hollow body 4 having a cavity 5, the cavity 5 able to be essentially filled with a system liquid 6 or a sample liquid 2. The movement unit 3 also includes a movement element 7, which acts on the cavity 5, for aspirating and/or dispensing the liquid 2, and a first drive element 8', which engages with a first drive 8, for displacing the movement element 7 during aspirating and/or dispensing. Furthermore, the movement unit 3 includes a pulse generator 9 for generating pressure waves in one of the liquids 2, 6 in the cavity 5 during dispensing, a liquid line 10, which the cavity 5 discharges into, and a pipette tip 11 or an adapter 12 for receiving a disposable pipette tip 11'. In this case, the liquid line 10 changes over to the adapter 12 and/or the pipette tip 11, 11' or the liquid line 10 includes the pipette tip 11 and/or the adapter 12.

The movement unit 3 is positioned on a carrier unit 13 so it is movable at least in the direction of an X, Y, or Z spatial axis, the carrier unit 13 including at least one second drive element 14', which is engaged with a second drive 14, for moving the movement unit 3 in the direction of an X, Y, or Z spatial axis. The carrier unit 13 also includes a flush line 15 for flushing and/or filling the cavity 5 in a direction preferably independent of the pipette tip. The hollow body 4 includes a flush inlet 16 which discharges into the cavity 5 and—because of its movability in the direction of an X, Y, or Z spatial axis—is implemented for connecting and disconnecting flush line 15 and flush inlet 16.

For pipetting of small volumes, the pipette tips 11, 11' are only filled in their forwardmost region with a specific volume of sample liquid 2 (aspiration), which may be dispensed again as a whole or in partial steps (dispensing). In such cases, the cavity 5 is preferably essentially filled with a system liquid 6, so that the pulses emitted by the pulse generator 9 onto the system liquid may propagate undamped up to the outlet opening of the pipette tip 11, 11' and therefore may cause the droplet breakaway or the droplet ejection. The system liquid 6 is preferably filled via the flush line 15 and the flush inlet 16, which significantly facilitates the elimination (flushing out) of air bubbles from the cavity 5.

For dispensing only, the cavity 5, the liquid line 10, the adapter 12, and/or the pipette tip 11, 11' are preferably filled with a sample liquid 2 via the flush line 15 and the flush inlet 16. The sample liquid 2 is subsequently dispensed by the interaction of movement element 7 and pulse generator 9, or solely by the pulse generator 9.

The flush line 15 in the carrier unit 13 and the flush inlet 16 of the hollow body 4 do not have to be constantly connected to one another, because the content of the pipette tip 11, 11' and/or of the cavity 5 is typically sufficient for dispensing many volume units. It is therefore sufficient to connect flush line 15 and flush inlet 16 to one another sporadically, to fill the cavity 5 and to flush the cavity. For this purpose, the entire movement unit 3 is implemented so it is movable in the direction of an X, Y, or Z spatial axis, i.e., flush line 15 and flush inlet 16 may be connected to one another or disconnected from one another through a movement in at least one of these directions. In this simplest case, the movement unit 3 is implemented as a slide valve; the flush inlet may also have an additional valve 17 for opening and closing the flush inlet 16 (cf. FIG. 14).

In this first embodiment, shown in FIG. 1, the pulse generator 9 is implemented as a pre-tensioned piezostack 26 and/or the movement element 7 is implemented as a piston 23, which is positioned so it is movable in a cavity 5 implemented as a cylindrical space 24. The rear end 25 of the piston 23 has approximately the same area as the piezostack 26 and is connected thereto. The rear end 27 of the piezostack is connected to the first drive element 8', which is implemented as a toothed rack and is in turn engaged with the first drive 8 and may be raised or lowered via its rotation. The piezostack 26 preferably includes a retracting spring 9', so that it may move the piston 23 back into its original position after the actuation of the pulse generator 9. In order that the drive element 8' may be moved without play, it includes a spring system 8' in relation to the carrier unit 13. The spring system 8" may be implemented in the scope of what is typical for mechanical systems, e.g., as a mechanical, pneumatic, hydraulic, or magnetic spring system.

The second drive 14 is engaged with the second drive element 14', which is implemented as a toothed rack on the outer surface 18 of the hollow body 4. The cylindrical space 24 changes without a transition over to the liquid line 10 and the adapter 12, upon which a disposable pipette tip 11' is placed. Notwithstanding this illustration, the adapter 12 itself may be implemented as a pipette tip (cf. FIGS. 2–11).

The carrier unit 13 essentially encloses the movement unit 3, due to which movement unit 3 and carrier unit 13 are at least partially implemented as coaxial tubes. This construction unifies all parts of the device according to the present invention in the smallest space. The flush line is molded into a ring 36, which is implemented to form a seal (not shown) in relation to the hollow body 4, in the region of the carrier unit 13. As shown here, sealing means 20 (e.g., in the form of O-rings) may be positioned between the outer surface 18 of the hollow body 4 and the inner surface 19 of the carrier unit: the movement unit 3 is implemented here as a slide valve which is movable perpendicularly (in the Z direction).

This simple device for aspirating and/or dispensing samples of the liquid preferably includes a controller for moving the piston 23 using the first drive 8 and/or the movement unit 3 using the second drive 14 and the pulses of the piezostack 26. This controller may be implemented as an external computer or may even be installed as an electronic component (chip) in the device and/or in a housing which receives the device (not shown). This controller is also used for synchronizing the movements of the first and second drives, so that the entire movement unit 3 may be moved in the Z direction and without any change of volume in the cylindrical space 24.

Figures 2, 3:
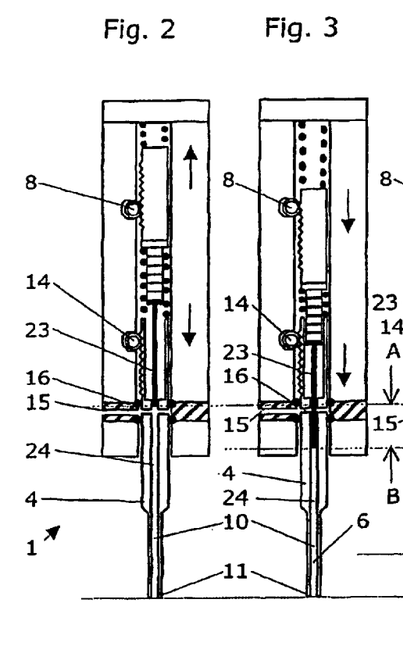
FIG. 2 shows the device according to the first embodiment in the "flush position"
FIG. 3 shows the device according to the first embodiment in the "conditioning position"

FIGS. 2 to 11 show preferred uses of the principle of the device 1 in a first embodiment, as shown in FIG. 1, for taking up and/or releasing samples of liquid:

In FIG. 2, the device 1 is in the "flush position". The piston 23 is pulled back using the first drive 8 to a level "A" (upper arrow) and releases the flush inlet 16, which is located in the rearmost region of the cylindrical space 24. The hollow body 4 is completely lowered (bottom arrow), so that the pipette tip assumes the lowermost level "F" reachable using the second drive 14. Flush line 15 and flush inlet 16 are aligned to one another and opened, so that from the rear and independently of the pipette tip, the entire cylindrical space 24, the liquid line 10, and the pipette tip 11 may be flushed out using system liquid and freed of air bubbles. The device 1 is preferably brought into a location "i" for this flushing, in which the system liquid may be collected again as it exits and reused. This location "i" defines a first X/Y position of the device.

In FIG. 3, the device 1 is in the "conditioning position". The piston 23 has been lowered using the first drive 8 all the way to a level "B" (upper arrow) and seals the flush inlet 16. The hollow body 4 is completely lowered (lower arrow), so that the pipette tip assumes the lowermost level "F", reachable using the second drive 14. Flush line 15 and flush inlet 16 are aligned to one another and open, so that—if necessary—some system liquid may be drawn along from the rear during the downward movement of the piston 23. The cylindrical space 24, the liquid line 10, and the pipette tip 11 are essentially filled with system liquid 6. The device 1 is preferably kept in the location "i" for this conditioning, in which the system liquid may be collected again as it exits and reused.

Figures 4, 5, 6:
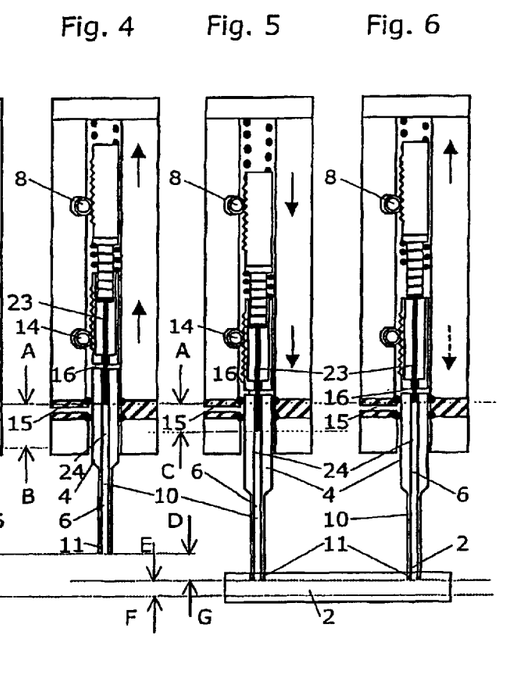
FIG. 4 shows the device according to the first embodiment in a first "transfer position"
FIG. 5 shows the device according to the first embodiment in a first "dip position"
FIG. 6 shows the device according to the first embodiment in the "aspiration position"

In FIG. 4, the device 1 is in a first "transfer position". The piston 23 is pulled back using the first drive 8 to a level "A" (upper arrow). The hollow body 4 is also pulled all the way back (lower arrow), so that the pipette tip assumes the uppermost level "D" reachable using the second drive 14. Flush line 15 and flush inlet 16 are now displaced in relation to one another and therefore closed. Through the synchronization of the two drives 8, 14 using a suitable controller (not shown), these positions may be assumed without the volume in the cylindrical space 24 changing. The cylindrical space 24, the liquid line 10, and the pipette tip 11 are therefore still filled with system liquid 6. The device 1 is subsequently brought into a location "ii", in which sample liquid is to be taken up. This location "ii" defines a second X/Y position of the device.

In FIG. 5, the device 1 is in a first "dip position". The piston 23 is lowered using the first drive 8 to the level "C" (upper arrow). The hollow body 4 is lowered by the same amount (lower arrow), so that the pipette tip assumes the level "E" and dips into the sample liquid 2 at the same time. Flush line 15 and flush inlet 16 remain displaced in relation to one another and therefore closed. Through the synchronization of the two drives 8, 14 using a suitable controller (not shown), these positions may be assumed without the volume in the cylindrical space 24 changing. The cylindrical space 24, the liquid line 10, and the pipette tip 11 are therefore still filled with system liquid 6 and the device 1 is ready to aspirate the sample liquid 2. The device 1 is in the location "ii", in which sample liquid is to be taken up. This location "ii" may be where a large container having sample liquid is located, but it may also be in the well of a microplate, for example, from which one single sample is to be taken up.

In FIG. 6, the device 1 is in the "aspirating position". The piston 23 is pulled back using the first drive 8 to the level "A" (upper arrow). The hollow body 4 is not moved and remains dipped into the sample liquid 2. Flush line 15 and flush inlet 16 remain displaced in relation to one another and therefore closed. Through the movement of only the first drive 8 using a suitable controller (not shown), the volume in the cylindrical space 24 is enlarged and therefore sample liquid 2 is aspirated into the pipette tip 11. The device 1 is in the location "ii". Alternatively to this position of the device 1 described, which is for aspiration of samples from large containers having a large liquid surface, for small containers having a small liquid surface, the movement unit 3 must be tracked on the sinking liquid surface. This is performed using a synchronized movement of the first and second drive elements 8', 14', driven via the drives 8 and 14.

Figure 7:
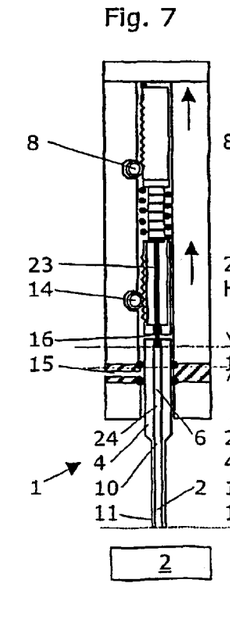
FIG. 7 shows the device according to the first embodiment in a second "transfer position"

In FIG. 7, the device 1 is in a second "transfer position". The piston 23 is pulled back to the level "H" using the first drive 8 (upper arrow). The hollow body 4 is raised by the same amount (lower arrow), so that the pipette tip assumes the level"I" and is pulled out of the sample liquid 2 at the same time. Flush line 15 and flush inlet 16 remain displaced in relation to one another and therefore closed. Through the synchronization of the two drives 8, 14 using a suitable controller (not shown), these positions may be assumed without the volume in the cylindrical space 24 changing. The cylindrical space 24, the liquid line 10, and the sample tip 11 are therefore still filled with system liquid 6 and/or sample liquid 2. The device 1 is subsequently brought into a location "iii", in which sample liquid is to be dispensed. This location "iii" may be where a collection container having sample liquid is located, but it may also be in the well of a microplate, for example, where one single sample is to be dispensed. This location "iii" defines a third X/Y position of the device.

Figures 8, 9, 10, 11:
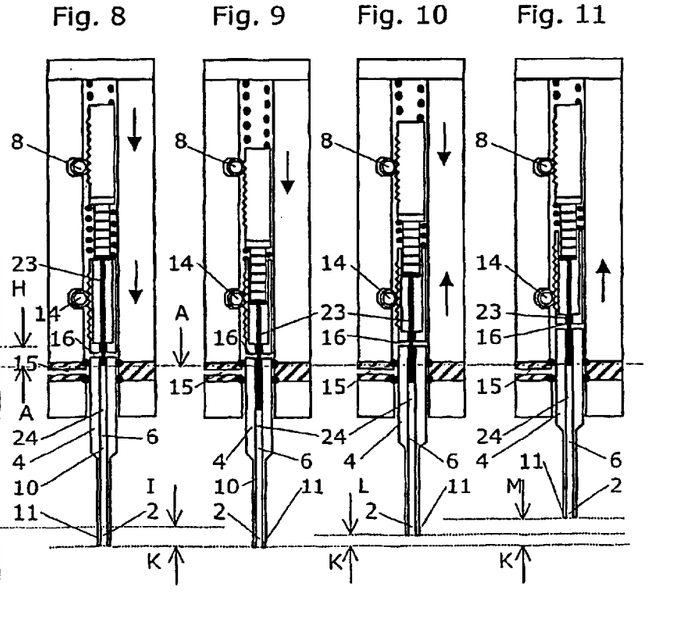
FIG. 8 shows the device according to the first embodiment in a second "dip position"
FIG. 9 shows the device according to the first embodiment in a first "dispensing position"
FIG. 10 shows the device according to the first embodiment in a second "dispensing position"
FIG. 11 shows the device according to the first embodiment in a third "dispensing position"

In FIG. 8, the device 1 is in a second "dip position". The piston 23 is lowered using the first drive 8 to the level "A" (upper arrow). The hollow body 4 is lowered by the same amount (lower arrow), so that the pipette tip assumes the level "K" and, at the same time, touches the surface of a liquid in front of it ("on liquid surface") or of the container, in particular the surface of the well of a microplate having 96, 384, or 1536 wells, for example, or the essentially flat surface of a target or a biochip ("on tip touch"); the level "K" may also be defined above the surface, however, for dispensing from the air ("from air"). Flush line 15 and flush inlet 16 remain displaced in relation to one another and therefore closed. Through the synchronization of the two drives 8, 14 using a suitable controller (not shown), these positions may be assumed without the volume in the cylindrical space 24 changing. The cylindrical space 24, the liquid line 10, and the sample tip 11 are therefore still filled with system liquid 6 and/or sample liquid 2, and the device 1 is ready for dispensing the sample liquid 2. The device 1 is in the location "iii".

In FIG. 9, the device 1 is in a first possible "dispensing position", in which the sample is to be dispensed using the pipette tip 11 by advancing the piston 23 (upper arrow) and simultaneously keeping the hollow body 4 still and therefore while maintaining the level "K". Typically, this is performed while dispensing of smaller or larger volumes "from air" or for dispensing small volumes "on tip touch", particularly for depositing small samples in an array and on the surface of fixed, essentially flat sample carriers or sample carriers having a structured surface, such as targets for "MALDI TOF-MS", "matrix assisted laser desorption ionization—time of flight mass spectrometry" or a biochip, i.e., on an essentially flat surface on which biological and/or organic and/or inorganic samples are positioned in an array.

In FIG. 10, the device 1 is in a second possible "dispensing position", in which the sample is to be dispensed by advancing the piston 23 (upper arrow) and simultaneously pulling back the hollow body 4 to a level "L" (lower arrow). This is typically performed during dispensing "on liquid surface" or "on tip touch", if a slow rise of the sample level may be expected. Through the synchronization of the two drives 8, 14 using a suitable controller (not shown), these positions may be assumed in such a way that the volume in the cylindrical space 24 changes continuously or in another way as desired. In particular, the pipette tip may always remain in contact with the surface of a liquid in front of it during the entire dispensation, without the outer surface of the pipette tip being wetted with the liquid in front of it.

In FIG. 11, the device 1 is in a third possible "dispensing position", in which the sample is to be dispensed by maintaining the level "A" of the piston 23 and simultaneously pulling back the hollow body 4 to a level "L" (lower arrow). This is typically performed during dispensing "on liquid surface", if a rapid rise of the sample level has to be expected. This may particularly be the case in very small wells of high-density microplates, if the pipette tip is always to remain in contact with the surface of a liquid in front of it during the entire dispensation.

During the dispensation as shown in FIGS. 8–11, the pulse generator 9 may be used for separating a dispensed droplet and/or volume or even for defining and ejecting a specific volume. Four modes of operation result from the description above:

A Large Volumes

The dispensing of volumes of more than one microliter is performed by advancing the movement elements 7, i.e., the piston 23 and/or wedges 33, and is determined solely by the advance of the first drive 8. Alternately, a pulse for "knocking out", to generate a droplet separation, may be emitted using the piezostack 26 and/or the piezo membrane 28'.

B Moderate Volumes

The dispensing of droplets between 0.5 and 1 µl is performed by advancing the movement elements 7, i.e., the piston 23 and/or wedges 33, and is determined by the first drive 8. The additional activation of the piezostack 26 and/or the piezo membrane 28' allows clean droplet separation. Furthermore, the following variants are possible:

B1 After the advance of the piston 23 and/or the wedge 33, the piezostack 26 and/or the piezo membrane 28' is actuated once in order to ensure the droplet separation from the air.

B2 Before the advance of the piston 23 and/or the wedge 33, the piezostack 26 and/or the piezo membrane 28' is actuated once in order to produce a defined separation edge in the pipette tip 11, 11'. The volume is defined by the advance of the piston 23 and/or the wedge 33 and the piezo activation allows droplet separation at the same point.

B3 During the entire advance of the piston 23 and/or the wedge 33, the piezostack 26 and/or the piezo membrane 28' is excited and the liquid stream is "chopped" into individual droplets. The volume is defined by the advance.

C Small Volumes

The dispensing of droplets of less than 0.5 µl is performed by the piezostack 26 and/or by the piezo membrane 28'. The advance of the movement elements 7, i.e., the piston 23 and/or the wedges 33, using the first drive 8, is used to compensate for the volumes dispensed. Ideally, the compensation is performed in such a way that the space which is defined by cylindrical space 24, piston 23 and/or membrane 28, 28', liquid line 10, adapter 12, and/or pipette tip 11, 11' is completely filled with a contiguous liquid column at least before the next pulse emitted. Therefore, if a device according to the present invention is used, the volume of a liquid sample dispensed is defined, for a given tip geometry, solely by the parameters of one single pulse generated by the pulse generator 9.

D Smallest Volumes

If the liquid column is pulled back slightly behind the tip opening, it becomes possible to accelerate single droplets of up to 10 nl out of a tip opening of up to 500 micrometers diameter using single pulses of the piezostack 26 and/or the piezo membrane 28'. For a constant opening diameter, the droplet volume is therefore only a function of the pulse strength.

Following these method steps, a further dispensation as shown in FIGS. 8–11 may occur or a flushing and conditioning step as shown in FIGS. 2–4 and/or a sample aspiration as shown in FIGS. 5–7 may be executed.

The special arrangement of hollow body 4, drives 8, 14, pulse generator 9, piston 23, cylindrical space 24, and adapter 12 and/or pipette tips 11, 11' allows an extremely narrow construction of the device 1, so that it is especially suitable for forming a component in a system for aspirating and/or dispensing liquid samples which includes multiple such devices 1. Such a system is, for example, a pipetting machine or (in the case of a system for dispensing samples) a dispensing machine. Such a system is preferably used for dispensing liquid into the wells of standard microplates having, for example, 96 wells, and/or the essentially flat surface of a target or a biochip (dispensing), or for aspirating liquids from one microplate and dispensing the samples into another microplate (pipetting). The reduction of the sample volumes (e.g., to fill high-density microplates having 384, 864, 1536 or even more wells) plays an increasingly important role, the precision of the sample volume dispensed having great significance. The time consumed for dispensing and/or transferring samples into these many wells is also significant. It is clear that multiple pipette tips which are operable in parallel reduce the time consumed for effective sample dispensing and/or for transferring by the same factor.

Because the arrangement of the wells in the microplates corresponds to a two-dimensional array, the components, hollow body 4, drives 8, 14, pulse generators 9, pistons 23, cylindrical spaces 24, and adapters 12 and/or pipette tips 11, 11' of a system are preferably also arranged in this way. In order to achieve compact construction, cylindrical spaces 24 and adapters 12 and/or pipette tips 11, 11' are positioned parallel to one another. An example of such an arrangement is illustrated in FIG. 12.

A disadvantage of most known multichannel systems is that volumes in the sub-microliter range may only be dispensed "on tip touch" or "on liquid surface", but not without contact (directly out of the air, "from air"). In contrast, a multichannel system according to the present invention allows the pipettable volumes to be reduced to the nanoliter range in any case.

Figure 12:
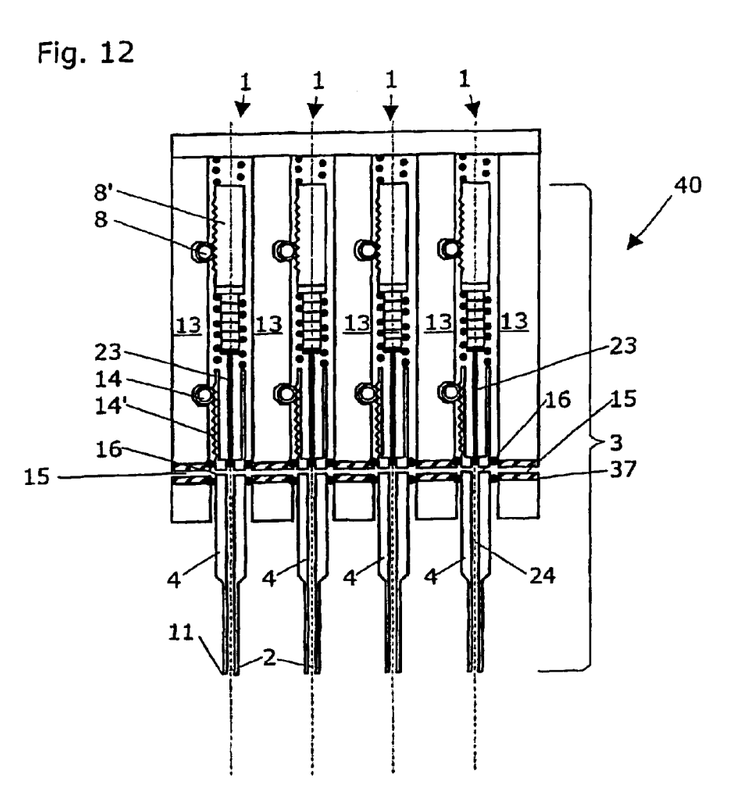
FIG. 12 shows a vertical partial section of a system having multiple devices according to the first embodiment in the "flush position"

FIG. 12 shows a vertical partial section of a system 40 having multiple devices 1, according to the first embodiment, in the "flush position" (cf. FIG. 2). In contrast to FIG. 2, in this case the movement units 3 run in a linear and/or flat matrix and/or in recesses of the carrier unit 13, these recesses—and therefore also the movement units 3—being positioned parallel to one another and next to one another in a line (one-dimensional array) or in a plane (two-dimensional array). The flush lines 15 may be positioned together in a plate 37 or may also be fed individually to each of the flush inlets 16 in the hollow body 4. However, all flush inlets are preferably positioned at the same height for a defined position of the piston 23, so that using a controller (not shown), all pistons of this linear or flat array—as needed—may be activated individually or in parallel. The flush liquid is preferably delivered at a specific pressure during the flush procedure, so that all cylindrical spaces 24 are sufficiently supplied.

Figure 13:
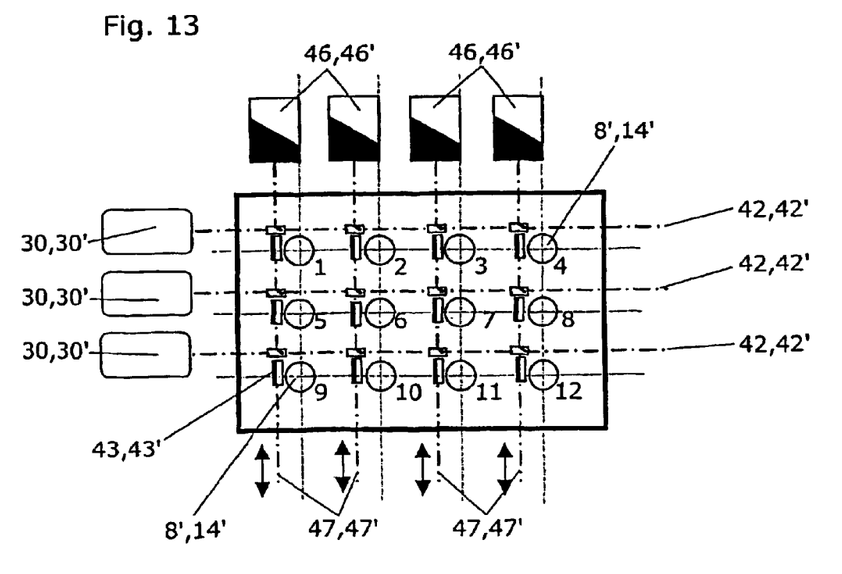
FIG. 13 shows a horizontal, very schematic partial section of the system in FIG. 12.

FIG. 13 shows a horizontal, very schematic partial section of the two-dimensional array, shown in FIG. 12, of a 12-channel system 40 for aspirating and/or dispensing samples of a liquid 2. Three drive shafts 42, which are each driven via a motor 30, lie in a first plane, which runs perpendicular to the drive elements 8', 14' positioned in parallel (numbered from 1 to 12). Each of these drive shafts 42 may be directly engaged with a first drive element 8' (not shown). Three drive shafts 42', which are each driven via a motor 30', also lie in a second plane, parallel to this first plane, which also runs perpendicularly to the drive elements 8', 14' arranged in parallel. Each of these drive shafts 42' may be directly engaged with a second drive element 14' (not shown). This simpler drive variation (not shown) allows the synchronized movement of one row 1–4, 2–8, or 9–12 of drive elements 8', 14' at a time. The power train from a drive shaft 42, 42' to a drive element 8, 14' is preferably implemented as a worm gear.

In accordance with the more complex drive variants illustrated in FIG. 13, selector shafts 47, 47', which run essentially perpendicular to the drive shafts 42, 42' and each of which is positioned so it is movable in the direction of its rotation axis (cf. double arrow), may lie somewhat above or below the first plane and the second plane. These selector shafts 47, 47' may be engaged with the drive shafts 42, 42' and the drive elements 8', 14' through simple displacement. Each displacement is caused by a switch 46, 46' which brings a selector shaft 47, 47' from a rest position (in which there is no interaction with the drive shafts 42, 42'; as shown) into an engagement position (not shown), in which a selector shaft 47, 47' is engaged with a drive shaft 42, 42'. In this case, such a switch 46, 46' may be implemented according to the solenoid, hydraulic, pneumatic, or another suitable principle. The engagement is produced in each case via a switch element 43, 43'. The power train from a drive shaft 42, 42' to a switch element 43, 43' and from there to the drive element 8', 14' is preferably implemented as a worm gear. A first variant of this more complex drive provides that the switch elements 43, 43' are rigidly connected to the selector shaft 47, 47' on which they are positioned. In this case, one single motor 30 and/or 30' may act on all drive elements 8' and/or 14', if all switch elements 43 and/or 43' are engaged with the drive shafts 42 and/or 42' and the drive elements 8' and/or 14'. Individual columns 1, 5, 9; 2, 6, 10; 3, 7, 11; or 4, 8, 12 may also each be moved selectively using one single motor.

The switch elements 43 and/or 43'—according to a second variant of this more complex drive—are preferably not rigidly connected to the selector shafts 47, 47'. In this case, single rows 1–4, 5–8, or 9–12 of the drive elements 8', 14' may be moved by engaging the switching elements 43, 43' with the drive shaft 42, 42' and by driving this row using a motor 30, 30'. However, it is also possible to activate and move single drive elements 8', 14' in an array in a targeted way. Of course, all drive elements 8, 14' of an array may also be moved simultaneously and synchronously. These special movement possibilities also apply for arrays which include significantly more pipetting or dispensing channels, e.g., 96, 384, or 1536 channels, and which are preferably positioned in a system for aspirating and/or dispensing samples of a liquid in such a way that the horizontal distribution and arrangement of the pipetting or dispensing channels precisely corresponds to the distribution and arrangement of the wells of microplates having, for example, 96, 384, or 1536 wells.

Figure 14:
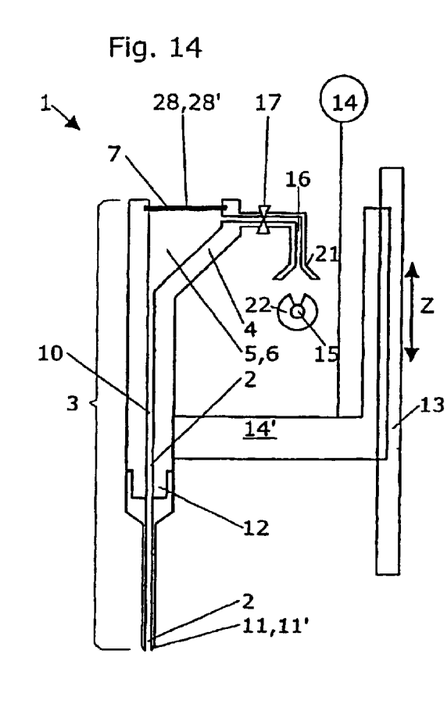
FIG. 14 shows a device for aspirating and/or dispensing liquid samples, according to a second embodiment, having a flush connection according to a first variant.

FIG. 14 shows a device for aspirating and/or dispensing liquid samples, according to a second embodiment, having a flush connection according to a first variant. This second embodiment is distinguished in that the movement element 7 for aspirating and/or dispensing liquid 2 includes a membrane 28, 28'. The device 1 for aspirating and/or dispensing samples of a liquid 2 includes a movement unit 3. This movement unit 3 includes a hollow body 4 having a cavity 5. The cavity 5 may be essentially filled with a system liquid 6 or a sample liquid 2. The membrane 28 which forms the movement element 7 may be implemented as a passive membrane 28 (cf. FIG. 16) or as an active membrane 28' (cf. FIG. 17) and acts on the cavity 5 to aspirate and/or dispense the liquid 2. A first drive element 8' (cf. FIGS. 16, 17) for displacing the movement element 7 during aspiration and/or dispensing is engaged with a first drive 8. A pulse generator 9 is used during dispensing to generate pressure waves in one of the liquids 2, 6 in the cavity 5, which discharges into a liquid line 10. The movement unit 3 also includes a pipette tip 11 or an adapter 12 to receive a disposable pipette tip 11', the liquid line 10 changing over to the adapter 12 and/or the pipette tip 11, 11' or including the pipette tip 11 and/or the adapter 12. The movement unit 3 is positioned on a carrier unit 13 and implemented so it is movable at least in the direction of an X, Y, or Z spatial axis. The carrier unit 13 includes—for moving the movement unit 3 in the direction of an X, Y, or Z spatial axis—at least one second drive element 14', which is engaged with a second drive 14. In addition, the carrier unit 13 includes a flush line 15 and the hollow body 4 includes a flush inlet 16 which discharges into the cavity 5. The hollow body 4 is implemented for connecting and disconnecting flush line 15 and flush inlet 16 as a result of its movability in the direction of an X, Y, or Z spatial axis. The hollow body 4 includes an additional valve 17 for opening and closing the flush inlet 16 in the region of the flush inlet 16. The flush inlet 16 includes a contact point 21, which is implemented so it may have an endpiece 22 of the flush line 15 applied to it using a movement of the hollow body 4 in the direction of an X, Y, or Z spatial axis to connect and disconnect flush line 15 and flush inlet 16. In the illustration of FIG. 14, which represents an especially preferred variant of the present invention, the movement unit 3 and therefore also the hollow body 4 is moved perpendicularly in the Z direction (cf. double arrow). The flush line 15 is preferably implemented as immovable, so that the movement unit 3 must be moved into a flush position, in order that flush line 15 and flush inlet 16 are connected to one another in this flush position of the device 1. As an alternative to this embodiment just described, the flush inlet 16—at least during the operation of the device 1—is directly and permanently connected to a supply line (not shown) for liquids (system or sample liquids).

Figure 15:
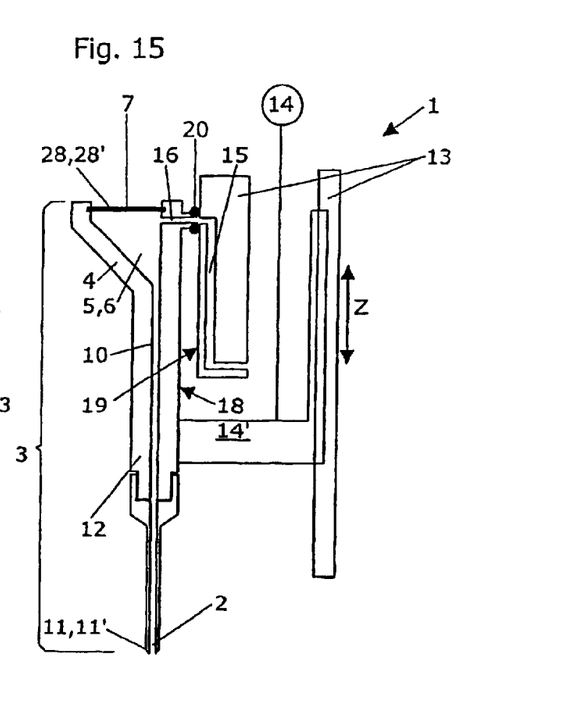
FIG. 15 shows a device for aspirating and/or dispensing liquid samples, according to a second embodiment, having a flush connection according to a second variant.

FIG. 15 shows a device 1 for aspirating and/or dispensing liquid samples, according to a second embodiment, which includes a membrane 28, 28' and a flush connection according to a second variant. The hollow body 4 is implemented for connecting and disconnecting flush line 15 and flush inlet 16 as a result of its movability in the direction of an X, Y, or Z spatial axis. The hollow body 4 is implemented as a slide valve for opening and closing the flush inlet 16 in the region of the flush inlet 16. Sealing means 20, e.g., in the form of lip seals, are positioned between a surface 18 of the hollow body 4 and a surface 19 of the carrier unit 13. In the illustration of FIG. 15, which also illustrates an especially preferred variant of the present invention, the movement unit 3, and therefore also the hollow body 4, are moved perpendicularly in the Z direction (cf. double arrow). The flush line 15 is preferably implemented as immovable, so that the movement unit 3 must be moved into a flush position, in order that flush line 15 and flush inlet 16 are connected to one another in this flush position of the device 1. In this embodiment just described, the flush line 15—at least during the operation of the device 1—is directly and permanently connected to a supply line (not shown) for liquids (system or sample liquids).

Notwithstanding the illustration in FIGS. 14 and 15, the movement for connecting and/or disconnecting flush line 15 and flush inlet 16 may be executed in any arbitrary direction, e.g., in the direction of the Y or X spatial axis or even in a direction deviating from these defined X, Y, or Z spatial axes.

Figure 16:
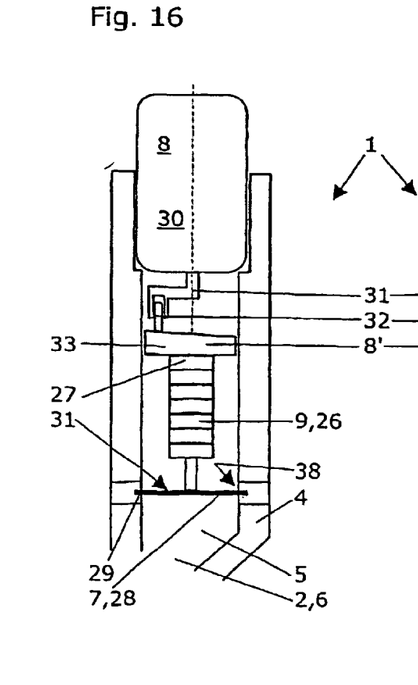
FIG. 16 shows a device for aspirating and/or dispensing liquid samples, according to a second embodiment, having a pulse generator according to a first variant.

FIG. 16 shows a device 1 for aspirating and/or dispensing liquid samples 2, according to a second embodiment, having a passive membrane 28 and a pulse generator 9 according to a first variant. The passive membrane 9 is connected around its circumference 29 to the inner wall 38 of the hollow body 4 and on its back 31 to a piezostack 26. This piezostack 26 is implemented as a pulse generator 9 for emitting pulses onto the passive membrane 28 and therefore onto the liquids 2, 6 in the cavity 5. The piezostack 26 is connected on its rear end 27 to a first drive 8 for raising and lowering the membrane 28, i.e., for aspirating and/or dispensing liquid 2. The first drive 8 preferably includes a DC motor having an encoder or a stepping motor, which acts on a wedge 33, attached to the rear end 27 of the piezostack 26, via a transfer part 31 connected to the motor 30 and a miniature bearing 32 attached thereto. The device 1 preferably includes a controller for moving the membrane 28 using the first drive 8 and/or the movement unit 3 using the second drive 14 and the pulses of the piezostack 26 and, if necessary, for controlling the valve 17.

Figure 17:
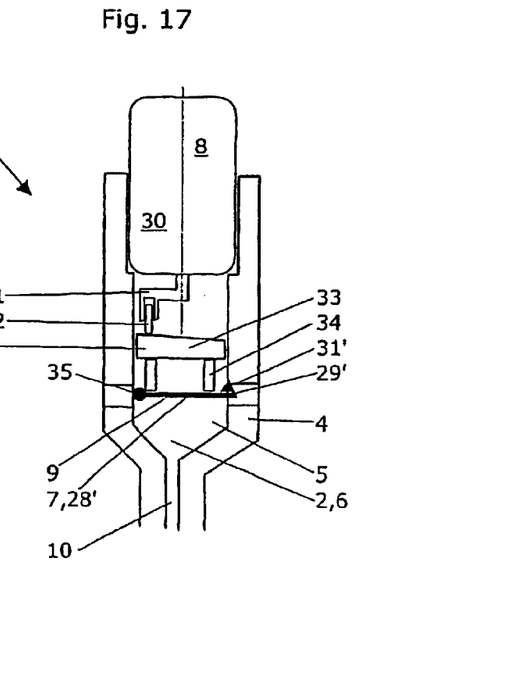
FIG. 17 shows a device for aspirating and/or dispensing liquid samples, according to a second embodiment, having a pulse generator according to a second variant.

FIG. 17 shows a device for aspirating and/or dispensing liquid samples, according to a second embodiment, having an active, bimorphous piezo membrane 28', implemented as a pulse generator 9 for emitting pulses onto the liquid 2 in the cavity 5, according to a second variant. The membrane 28' is connected on its rear side 31' or around its circumference 29' to a hollow cylinder 34, the hollow cylinder 34 supporting a wedge 33. The device 1 preferably includes a ring seal 35 which seals the cavity 5 between the circumference 29' of the active membrane 28' and the inner wall 38 of the hollow body 4. The first drive 8 preferably includes a DC motor having an encoder or a stepping motor, which acts on the wedge 33 attached to the hollow cylinder 34 via a transfer part 31 connected to the motor 30 and a miniature bearing 32 attached thereto. The device 1 preferably includes a controller for moving the wedge 33 using the first drive 8 and/or the movement unit 3 using the second drive 14 and the pulses of the piezo membrane 28' and, if necessary, for controlling the valve 17. All devices and/or systems shown may include a robot device or another device suitable for moving the devices and/or their arrays. This is particularly advantageous if the aspirating location of liquid is different from its dispensing location and the devices 1 must be moved in the X and/or Y and/or Z directions. The movement units 3 are preferably positioned, according to a first arrangement, parallel to the Z spatial axis and therefore perpendicular to the plane defined by the axes X and Y and thus form a linear array. In a second, alternative arrangement, the movement units 3 are positioned slanted in relation to the Z axis. Particularly for an embodiment of the system 40, using which 8, 16, or 32 samples are to be dispensed in a line, for example, the movement units 3 are alternately slanted positively or negatively in relation to the Z axis. Using this special arrangement of the movement units 3, the dispensing locations for the samples may lie closer to one another than would be possible using a linear array of movement units 3 positioned parallel to one another.

The elements corresponding to one another are provided with identical reference numbers in the figures, these reference numbers are not cited in every case in the text. Any arbitrary practical combination of the features disclosed in this document is included by the inventive idea. In particular, the features in FIGS. 1–13 and/or in FIGS. 14–17 may be combined in any arbitrary way.

What is claimed is:

1. A device for at least one of aspirating and dispensing samples of a liquid with a movement unit, the device comprising:

a hollow body having a cavity adapted to be essentially filled with a system liquid or a sample liquid, and having a movement element, acting on the cavity, for at least one of aspirating and dispensing the liquid;

a first drive element engaged with or capable of being engaged with a first drive for displacing the movement element during at least one of aspirating and dispensing the liquid;

a liquid line into which the cavity discharges;

a pipette tip or an adapter for receiving a disposable pipette tip, the liquid line changing over to the pipette tip or the adaptor or including the pipette tip or the adapter;

a flush line, the hollow body including a flush inlet which discharges from the flush line into the cavity;

a carrier unit for moving the movement unit which is movably attached to the carrier unit in the direction of at least one of an X, or a Y, or a Z spatial axis, the carrier unit including at least one second drive element which is engaged with a second drive; and wherein the movement unit comprises the hollow body and the movement element, the first drive element, the second drive element, and the pipette tip or the adapter, as well as a pulse generator for generating pressure waves the liquid in the cavity during dispensing, all these elements being movable together in at least one direction of the X, or the Y, or the Z spatial axis with respect to the carrier unit.

2. The device of claim 1, wherein the second drive element is implemented as a toothed rack on the outer surface of the hollow body.

3. The device of claim 1, wherein the hollow body, because of movability in at least one direction of the X, or the Y, or the Z spatial axis with respect to the carrier unit, is implemented for connecting and disconnecting the flush line and flush inlet as a slide valve in the region of the flush inlet or includes an additional valve there for opening and closing the flush inlet.

4. The device of claim 1, including sealing means positioned between a surface of the hollow body and a surface of the carrier unit.

5. The device of claim 1, wherein the flush inlet includes a contact point which is implemented so that an endpiece of the flush line is applied to the contact point using a movement of the hollow body in at least one direction of the X, or the Y, or the Z spatial axis to connect and disconnect the flush line and flush inlet.

6. The device of claim 1, wherein the movement element for at least one of aspirating and dispensing liquid is implemented as a piston and the cavity is implemented as a cylinder, the rear end of the piston being connected to a piezostack which is implemented as the pulse generator for emitting pulses onto the piston and therefore onto the liquids in the cavity, and the rear end of the piezostack is connected to the first drive element for raising and lowering the piston.

7. The device of claim 6, including a controller for moving the piston using the first drive or for moving the movement unit using the second drive, or for moving both drives for synchronizing the drives and for controlling the pulses of the piezostack.

8. The device of claim 1, wherein the movement element includes a membrane.

9. The device of claim 8, wherein the membrane is a passive membrane which is connected around its circumference to the inner wall of the hollow body and, on a rear side of the membrane, the membrane is connected to a piezostack which is implemented as the pulse generator for emitting pulses onto the passive membrane and therefore onto the liquid in the cavity, a rear end of the piezostack being connected to the first drive for raising and lowering the membrane.

10. The device of claim 9, wherein the first drive includes a DC motor having an encoder or a stepping motor, which acts on a wedge attached to the rear end of the piezostack via a transfer part connected to the motor and a miniature bearing attached to the transfer part.

11. The device of claim 10, including a controller for moving the membrane using the first drive or for moving the movement unit using the second drive, or for moving both drives, and pulses of the piezostack.

12. The device of claim 8, wherein the membrane is an active, bimorphous piezo membrane which is implemented as the pulse generator for emitting pulses onto the liquid in the cavity.

13. The device of claim 12, wherein the rear side or the circumference of the membrane is connected to a hollow cylinder which supports a wedge.

14. The device of claim 13, including a ring seal which seals the cavity between the circumference of the active membrane and the inner wall of the hollow body.

15. The device of claim 13, wherein the first drive includes a DC motor having an encoder or a stepping motor, which acts on the wedge attached to the hollow cylinder via a transfer part connected to the motor and a miniature bearing attached thereto.

16. The device of claim 15, including a controller for moving the wedge using the first drive or for moving the movement unit using the second drive, or for moving both drives, and pulses of the piezo membrane.

17. A system for at least one of aspirating and dispensing samples of a liquid, wherein the system includes one or more devices according to claim 1.

18. The system of claim 17, including a robot for moving the devices in at least one of the X, or the Y, or the Z direction.

19. The system of claim 17, including first drives and second drives having shafts which are implemented to engage, via switch elements, on the first drive element or on the second drive element, or on both drive elements, of the individual devices, or of linear groups, or of two-dimensional arrays of the devices.

20. The system of claim 19, wherein the linear the groups include 4, 8, 12, 16, 24, or 32 devices, and wherein the arrays include 16, 32, 96, 384, or 1536 devices.

21. The system of 17, including switches for linear displacement of selector shafts, which, depending on position, are engagable with the shafts of the drives or with the drive elements, or which are engagable with the shafts of the drives and with the drive elements.

22. A method of using a device according to claim 1, comprising pipetting or dispensing samples of a liquid.

23. The method of claim 22, wherein samples of a liquid are pipetted or dispensed in wells of a microplate.

24. The method of claim 22, wherein samples of a liquid are pipetted or dispensed on the surface of a target for sample investigation, particularly a MALDI TOF-MS target or a biochip.

* * * * *